United States Patent
Odom

(10) Patent No.: US 8,722,106 B2
(45) Date of Patent: May 13, 2014

(54) LIP BALM COMPOSITION

(75) Inventor: Fountain Odom, Charlotte, NC (US)

(73) Assignee: The MotherVine Nutraceuticals Co. LLC, Charlotte, NC (US)

( * ) Notice: Subject to any disclaimer, the term of this patent is extended or adjusted under 35 U.S.C. 154(b) by 296 days.

(21) Appl. No.: 13/309,736

(22) Filed: Dec. 2, 2011

(65) Prior Publication Data

US 2013/0142881 A1 Jun. 6, 2013

(51) Int. Cl.
- *A61K 36/00* (2006.01)
- *A61K 36/87* (2006.01)
- *A61K 35/64* (2006.01)
- *A61K 31/20* (2006.01)

(52) U.S. Cl.
USPC ............ 424/725; 424/766; 424/538; 514/558

(58) Field of Classification Search
USPC .......................... 424/725, 766, 538; 514/558
See application file for complete search history.

(56) References Cited

U.S. PATENT DOCUMENTS 4,793,991 A * 12/1988 Slimak ........................... 424/64

FOREIGN PATENT DOCUMENTS

| DE | 102008021756 A1 | * 11/2009 |
| DE | 102011101512 A1 | * 11/2012 |
| SU | 1183109 A | * 10/1985 |

OTHER PUBLICATIONS

English translation of Abstract of SU 1183109 A1, Lobanova et al.*

* cited by examiner

*Primary Examiner* — Rosanne Kosson
(74) *Attorney, Agent, or Firm* — Clements Bernard PLLC; Gregory N. Clements

(57) ABSTRACT

A lip balm composition of natural ingredients, comprising: 54-70 wt. % of one or more oils, 22-28 wt. % beeswax, 3-4 wt. % propolis, 3-5 wt. % pomace, 0.02-3.2 wt. % antioxidant, and optional ingredients, whereby all components add to 100 wt. %.

15 Claims, No Drawings

LIP BALM COMPOSITION

FIELD OF THE INVENTION

The present invention pertains to a lip balm composition based on natural products of the honeybee and muscadine grapes. More specifically, the lip balm composition is based on vegetable oil, essential oils or other organic oils, beeswax, propolis, and honey, and muscadine pomace. These ingredients are all natural products.

BACKGROUND OF THE INVENTION

Lip balms are well known in the marketplace and can be purchased at any drug store, department store, grocery store, etc. These products are sold under such names as Burt's Bees®, Chapstick®, Carmex® and Blistex®. These products are made of a blend of a one or more oils and wax as the majority ingredients. Recently there is more tendency toward natural ingredients rather than using fillers, oil based products such as paraffin wax, and synthetic flavors and scents.

SUMMARY OF THE INVENTION

The lip balm composition of the present invention comprises 54 to 70 wt. % of one or more natural oils, 22-28 wt. % bee's wax, 3-4 wt. % propolis, 3-5 wt. % pomace, and a protective amount of antioxidant to protect the oil from spoiling and other optional ingredients such as natural scents, flavorings, coloring, UV protectors and vitamins.

The lip balm is produced by mixing the less volatile ingredients together such as oil, wax, pomace, propolis, antioxidants and other ingredients together. One or more of these ingredients are solid at room temperature and thus these ingredients are melted and mixed together at about 60-80° C. Once the less volatile ingredients are thoroughly mixed together, and cooled to about room temperature, the more volatile natural ingredients are blended with less volatile components. These ingredients primarily are natural scented oils.

DESCRIPTION OF THE PREFERRED EMBODIMENTS

The majority component of the lip balm composition of the present invention is one or more oils. For lip balm compositions, various oils are suitable such as natural essential oils, other natural organic oils including vegetable oil, citris oil, plant oil, fish oil, non-citris fruit oil, oils having flavors, perfume or scents, etc. Suitable vegetable oils may be canola oil, corn oil, neem oil, olive oil, cottonseed oil, coconut oil, palm oil, nut oils, safflower oil, sesame oil, soybean oil, and sunflower oil. Nut oils can be peanut oil, almond oil, cashew oil, hazelnut oil, macadamia oil, pecan oil, pine nut oil, pistachio oil, and walnut oil. Citrus oils can include grapefruit seed oil, lemon oil, orange oil, tangerine oil, lime oil, mandarin oil, and the like. Other oils based on fruits, plants and fish would include fish oil such as omega 3 oil, flaxseed oil (linseed oil), apricot oil, avocado oil, cocoa butter oil, coconut oil, hemp oil, papaya seed oil, rice bran oil, shea butter oil, tea tree seed oil, and wheat germ oil. Other oils can include lavender oil, rosemary oil, tung oil, jojoba oil, poppy seed oil, castor oil, mango oil, rose hip oil, tall oil. Essential oils can include chamomile oil, cinnamon oil, citronella oil, eucalyptus oil, fennel seed oil, jasmine oil, juniper berry oil, lavender oil, lemon grass oil, nutmeg oil, patchouli oil, peppermint oil, pine oil, rose oil, rose hip oil, rosemary oil, rosewood oil, sandalwood oil, sassafras oil, spearmint oil, and wintergreen oil. The preferred oil is olive oil as the major component.

Wax that is typically used in lip balm compositions can include beeswax as well as carnauba wax (palm wax), coconut wax, and soy wax.

Pomace is the solid remains of grapes, olives, apples or other fruits after pressing for the juice or oil. It contains the skins, the pulp, the seeds, etc. Apple pomace, various grape pomaces, and olive pomace are known in the industry. Preferred for the present invention is muscadine grape pomace. Resveratrol is found in the skin of red grapes and in other fruits, and is said to have beneficial health factors. Muscadine contains comparatively high amount of resveratrol.

It is known that various oils and waxes can become rancid via oxidation. Temperature change, for example, can oxidize some oils and waxes to destroy the odor, and can break down into undesired components. Therefore, it is important that an antioxidant be employed. A very good antioxidant is vitamin E. Vitamin E comes in a few different forms such as vitamin E acetate, or vitamin E itself, including tocotrienol and tocopherol, as well as vitamin C (ascorbic acid), and vitamin A (retinol). Salicylic acid, fructose, uric acid and certain essential oils are rich in antioxidant properties. Preferred for the present invention is vitamin E in one or more of its forms.

The lip balm composition of the present invention comprises 54 to 70 wt. % of one or more natural oils, 22-28 wt. % bee's wax, 3-4 wt. % propolis, 3-5 wt. % pomace, and a protective amount of antioxidant to protect the oil from spoiling and other optional ingredients such as natural scents, flavorings, coloring, UV protectors and vitamins. More particularly, the lip balm composition of the present invention comprises natural ingredients having a lower volatility such as 54-66% wt. % olive oil, 22-28 wt. % beeswax, 3-5 wt. % pomace, 3-4 wt. % propolis, 1.6-2.4 wt. % honey, 1.6-2.4 wt. % apricot oil, 1.6-2.4 wt. % vitamin E acetate, 0.02-0.08 wt. % vitamin E, and the natural ingredients having more volatile components such as 0.5-1.5 wt. % lavender oil, 0.3-0.7 wt. % rosemary oil, 0.3-0.7 wt. % neem oil, wherein all ingredients add up to 100 wt. %.

Of the above components, all lower volatility components can be uniformly mixed together except for the higher volatility components of lavender oil, rosemary oil and neem oil. Accordingly, the olive oil, beeswax, pomace, propolis, honey, apricot oil, vitamin E acetate and vitamin E are blended together forming a uniform mixture, when all these components are in a liquid state, typically about 60 to 80° C. Then the three more volatile components of lavender oil, rosemary oil and neem oil may be blended together and mixed with the lower volatile blended mixture, or each one of the 3 components can be blended with the mixture sequentially in any order, forming the lip balm of the present invention. Preferably the total blend is then introduced into a typical lip balm container while still in liquid form. Thereafter, these components are cooled, preferably to about room temperature where the total blend solidifies.

Thus, it appears that there is provided, in accordance with the invention, a lip balm composition that fully satisfies the objects, aims, and advantages set forth above set forth above. While the invention has been described in conjunction with specific embodiments hereof, it is evident that many alternatives, modifications, and variations will be apparent to those skilled in the art in light of the foregoing description. Accordingly, it is intended to embrace all such alternatives, modifications and variations that fall within the spirit and the broad scope of the appended claims.

What is claimed is:

1. A lip balm composition comprising:
   54-70 wt. % of one or more oils,
   22-28 wt. % beeswax,
   3-4 wt. % propolis,
   3-5 wt. % pomace,
   0.02-3.2 wt. % antioxidant, and
   optional ingredients, whereby all components add to 100 wt. %.

2. The lip balm composition of claim 1, wherein said oil is olive oil.

3. The lip balm composition of claim 2, wherein said olive oil is present at 54-66 wt. %.

4. The lip balm composition of claim 2, wherein said oil further includes oils for skin softening, flavor or scent.

5. The lip balm composition of claim 1, wherein said oils are one or more of olive oil, apricot oil, vegetable oil, lavender oil, rosemary oil, or a mixture of 2 or more of these.

6. The lip balm composition of claim 5, wherein said vegetable oil is neem oil.

7. The lip balm composition of claim 5, wherein said oil or oils are present at 54-66 wt. %.

8. The lip balm composition of claim 7 further comprising other oils, wherein the other oils are present at 0.5-5.3 wt. %.

9. The lip balm composition of claim 1, wherein said antioxidant is vitamin E.

10. The lip balm composition of claim 1, further containing honey.

11. The lip balm composition of claim 10, wherein said honey is present at 1.6-2.4 wt. %.

12. A lip balm composition comprising:
    54-66 wt. % olive oil, 22-28 wt. % beeswax, 3-5 wt. % pomace, 3-4 wt. % propolis, 1.6-2.4 wt. % honey, 1.6-2.4 wt. % apricot oil, 1.6-2.4 wt. % vitamin E acetate, 0.5-1.5 wt. % lavender oil, 0.3-0.7 wt. % rosemary oil, 0.3-0.7 wt. % vegetable oil, and 0.02-0.08 wt. % vitamin E, whereby all ingredients add to 100 wt. %.

13. The lip balm composition of claim 12, wherein said vegetable oil is neem oil.

14. A method of making a lip balm comprising:
    i) mixing olive oil, beeswax, pomace, propolis, honey, apricot oil and vitamin E together,
    ii) mixing lavender oil, rosemary oil and neem oil together, and
    iii) mixing i) and ii) together,
    wherein the olive oil is present at 54-56 wt. %, the beeswax is present at 22-28 wt. %, the pomace is present at 3-5 wt. %, the propolis is present at 3-4-wt. %, the honey is present at 1.6-2.4 wt. %, the apricot oil is present at 1.6-2.4 wt. %, the vitamin E is present at 0.02-3.2 wt. %, the lavender oil is present at 0.5-1.5 wt. %, the rosemary oil is present at 0.3-0.7 wt. %, and the neem oil is present at 0.3-0.7 wt. %, whereby all ingredients add to 100 wt. %.

15. The method of claim 14, wherein said vitamin E is present as a mixture of vitamin E acetate and a blend of vitamin E and vegetable oil.

* * * * *